United States Patent [19]

Rescalli

[11] Patent Number: 5,750,780
[45] Date of Patent: May 12, 1998

[54] PROCESS FOR THE SYNTHESIS OF UREA COMPRISING TWO SEPARATE REACTION ZONES

[75] Inventor: Carlo Rescalli, S. Donato Milanese, Italy

[73] Assignee: Snamprogetti S.p.A., S. Donato Milanese, Italy

[21] Appl. No.: 577,182

[22] Filed: Dec. 22, 1995

[30] Foreign Application Priority Data

Jun. 30, 1995 [IT] Italy .................... MI95A1402

[51] Int. Cl.$^6$ .................................. C07C 273/04
[52] U.S. Cl. .................. 564/67; 564/66; 564/70; 564/71; 564/72
[58] Field of Search ................. 564/66, 67, 70, 564/71, 72

[56] References Cited

U.S. PATENT DOCUMENTS 4,208,347  6/1980  Pagani .......................... 564/67

FOREIGN PATENT DOCUMENTS 1538285  7/1968  France .
1196657  7/1970  United Kingdom .
96/23767  8/1996  WIPO .

Primary Examiner—Shailendra Kumar
Attorney, Agent, or Firm—Oblon, Spivak, McClelland, Maier & Neustadt, P.C.

[57] ABSTRACT

A process for the synthesis of urea starting from ammonia and carbon dioxide, comprising a reaction step carried out in at least two distinct operating zones basically at the same pressure, but having a different operating temperature, the difference being preferably between 5° and 60° C., and subsequent separation steps of the non-converted reagents, wherein a gaseous stream is transferred from the first zone, at a higher temperature, to the second zone, at a lower temperature, and a liquid stream, containing urea and/or ammonium carbamate, is transferred from the second zone to the first, so that said gaseous stream is preferably at least 5% by weight with respect to the stream effluent from the first zone to the subsequent separation steps. This process allows a ratio urea/(urea+carbamate), in the stream leaving said reaction step, of more than 70%, to be obtained.

54 Claims, 4 Drawing Sheets

PROCESS FOR THE SYNTHESIS OF UREA COMPRISING TWO SEPARATE REACTION ZONES

BACKGROUND OF THE INVENTION

1. Field of the Invention

The present invention relates to a process for the synthesis of urea comprising two separate reaction zones.

In particular, the present invention relates to a process with a high conversion for the synthesis of urea, comprising the reaction of ammonia and carbon dioxide in at least two separate steps basically at the same high pressure, the subsequent separation of urea from the mixture containing the non-reacted products and the recycling of these to at least one of the reaction steps.

2. Description of the Background

Urea is a widely used industrial product especially adopted as a fertilizer, although it is also used in the farmaceutical field and that of polymeric materials (urea-formaldehyde resins).

All the industrial processes for the preparation of urea are practically based on direct synthesis according to the complete reaction:

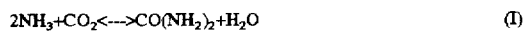

$$2NH_3 + CO_2 \longleftrightarrow CO(NH_2)_2 + H_2O \tag{I}$$

This takes place in two distinct reaction steps with the formation of ammonium carbamate as an intermediate:

$$NH_3 + CO_2 \longleftrightarrow (NH_2)COONH_4 \tag{1a}$$

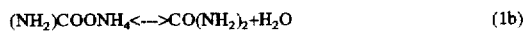

$$(NH_2)COONH_4 \longleftrightarrow CO(NH_2)_2 + H_2O \tag{1b}$$

In the first step (1a) there is an exothermic reaction the equilibrium of which moves towards the right at room temperature (formation of ammonium carbamate), which necessitates however high pressures to reach an equilibrium which is favourable at the high temperatures required to carry out the subsequent step (1b) with a satisfactory yield. In the second step (1b), there is an endothermic reaction which only at high temperatures (>150° C.) reaches a satisfactory rate for the industrial application of the process, with an equilibrium state which, however, results in a conversion of the $CO_2$ of not more than 53% in a stoichiometric mixture of the reagents at 185° C. This unsatisfactory conversion can be conveniently raised by increasing the ratio $NH_3/CO_2$, but is further reduced by the addition of water. The latter also has an unfavourable effect on the total kinetics of the process.

Normally, the two above reaction steps occur contemporaneously in the same reactor, and the reaction mixture therefore comprises urea, water, ammonia, carbon dioxide and ammonium carbamate, with a relative concentration, in the different points of the reactor, depending on the various thermodynamic and kinetic factors which contribute to the process.

Processes of this kind for the production of urea have been amply indicated and described in specific literature in the field. A detailed report of the most common processes for the production of urea can be found, for example, in the publication "Encyclopedia of Chemical Technology" Ed. Kirk-Othmer, Wiley Interscience, third ed. (1983), vol.23, pages 551–561.

In industrial processes for the production of urea the synthesis is normally carried out in a reactor fed with $NH_3$, $CO_2$ and aqueous solutions of ammonium carbonate (an unstable precursor of carbamate, $(NH_4)_2CO_3$) and/or carbamate coming from recycled streams of the non-converted reagents, at temperatures of between 170° and 200° C., at pressures of at least 130 ata, such that a liquid phase is normally generated, with a molar ratio $NH_3/CO_2$ of between 2.5 and 4.5, calculated on the sum of the feeding streams. The molar ratio $H_2O/CO_2$ being fed to the reactor is generally between 0.5 and 0.6. Under these conditions, the product discharged from the reactor has conversions of between 50 and 65% with respect to the $CO_2$ fed. As well as the water formed and the excess $NH_3$ fed, the effluent from the reactor still contains high quantities of non-converted $CO_2$, mainly in the form of non-converted ammonium carbamate.

The separation of the urea from these products is carried out in several operating sections at a high temperature and decreasing pressures, in which both the decomposition of the ammonium carbamate to $NH_3$ and $CO_2$ (products made available for recycling to the reactor) and the evaporation of the reaction water are carried out, to finally obtain urea with a high purity for the subsequent prilling step.

The section for the separation and recycling of the carbamate has investment costs which considerably influence the cost of the final product. From this section, all the $CO_2$ and part of the $NH_3$, since both are present contemporaneously, are made available for recycling as ammonium salts (carbonate and/or bicarbonate and/or carbamate depending on the temperature) making it necessary to use water as a solvent move them in order to avoid the precipitation of the salts and consequent blocking of the lines of interest. However, the recycle of water to the reactor can, in turn, decrease the conversion since it adversely affect reaction (1b). To explain the above more clearly, it should be pointed out that the quantity of water normally recycled to the reactor is approximately equal to that produced during the reaction, thus doubling the quantity of water inside the reactor. The traditional reactor is therefore particularly penalized owing to the high concentration of water right from the beginning of the reaction zone, which concentration further increase up to a maximum in the terminal zone of the reactor where, viceversa, it would be much more useful to have a concentration of water as lower as possible in order to induce conversion of the residual carbamate. Known processes which operate according to the above general scheme are, for example, described in U.S. Pat No. 4,092,358, U.S. Pat. No. 4,208,347, U.S. Pat. No. 4,801,745 and U.S. Pat. No. 4,354,040.

In order to increase the conversion of carbon dioxide into urea, synthesis processes of urea have been proposed comprising at least two reaction zones which are separate from each other and operating under different conditions of temperature and pressure. The published European patent application 544,056 describes, for example, a process in which there are two independent reaction zones both fed with ammonia and carbon dioxide, of which one operates in the traditional way and the other at even higher temperatures and pressures, more than 200° C. and 300 bars respectively. Although this does in fact allow an increase in the total conversion per passage, the use of such high pressures and temperatures in the second reaction zone creates problems of safety and corrosion of the equipment involved, thus requiring greater investment and higher maintenance costs.

There is consequently still a high demand for processes for the production of urea with an increased productivity in combination with lower energy consumption and investment and maintenance costs, especially if we consider that for a product having such a wide use and a corresponding low added value, it is necessary in practice to have plants of large dimensions capable of producing up to 2000 tons of urea a day, in which improvements in the yields and/or unit energy consumption, even if apparently not very significant, can provide great economical advantages.

The Applicant has now found a process which overcomes the difficulties and limitations of the traditional industrial processes mentioned above, also without requiring the use of extremely high pressures, reaching conversions by passage of $CO_2$ into urea of more than 65% and normally between 70 and 85% depending on the operating conditions and plant scheme used.

SUMMARY OF THE INVENTION

The present invention therefore relates to an improved process for the synthesis of urea from ammonia and carbon dioxide with the formation of ammonium carbamate as intermediate, comprising:

(a) reacting, in a reaction step, ammonia and carbon dioxide at a total pressure of between 90 and 250 ata, with a molar ratio $NH_3/CO_2$, as such or in the form of ammonium carbamate, of between 2.1 and 10, preferably between 2.1 and 6.0, with the formation of a first liquid mixture containing urea, ammonium carbamate, water and ammonia, (b) transferring said first liquid mixture to at least one decomposition-stripping step;

(c) heating said first liquid mixture in said decomposition-stripping step, operating basically at the same pressure used in the previous step (a), to obtain the decomposition of at least a part of the ammonium carbamate contained therein, with the formation of a first gaseous mixture containing ammonia and carbon dioxide, and a second liquid mixture containing urea, water, ammonia and the non-decomposed part of the ammonium carbamate;

(d) transferring at least a part of said first gaseous mixture to at least one condensation step operating basically at the same pressure as step (a) and condensing the transferred mixture with the formation of a third liquid mixture containing ammonium carbamate, water and ammonia;

(e) transferring said third liquid mixture and the remaining part of the first gaseous mixture to the reaction step (a);

(f) recovering the urea contained in the second liquid mixture in one or more subsequent decomposition, condensation and separation steps to obtain basically pure urea and recycling to the synthesis the non-converted ammonia and carbon dioxide (as such or in the form of ammonium carbamate); characterized in that:

the above reaction step (a) is carried out in at least two distinct zones, communicating with each other and maintained basically at the same pressure, of which the first operates at temperatures of between 170° and 230° C. with the formation of said first liquid mixture and a second prevalently gaseous mixture basically containing ammonia, water, carbon dioxide and, eventually, inert gases, and the second zone operates at a lower temperature than the first one, so that at least 5% by weight of the second prevalently gaseous mixture, with respect to the weight of the above first liquid mixture, preferably a quantity equal to or more than 10% by weight, more preferably, in a quantity of between 20 and 40% by weight, is transferred from the first to the second zone, with the subsequent formation, in the latter, of a further liquid mixture containing, ammonia, ammonium carbamate and, eventually, urea, which is again transferred from the second to the first reaction zone.

Figure 1:
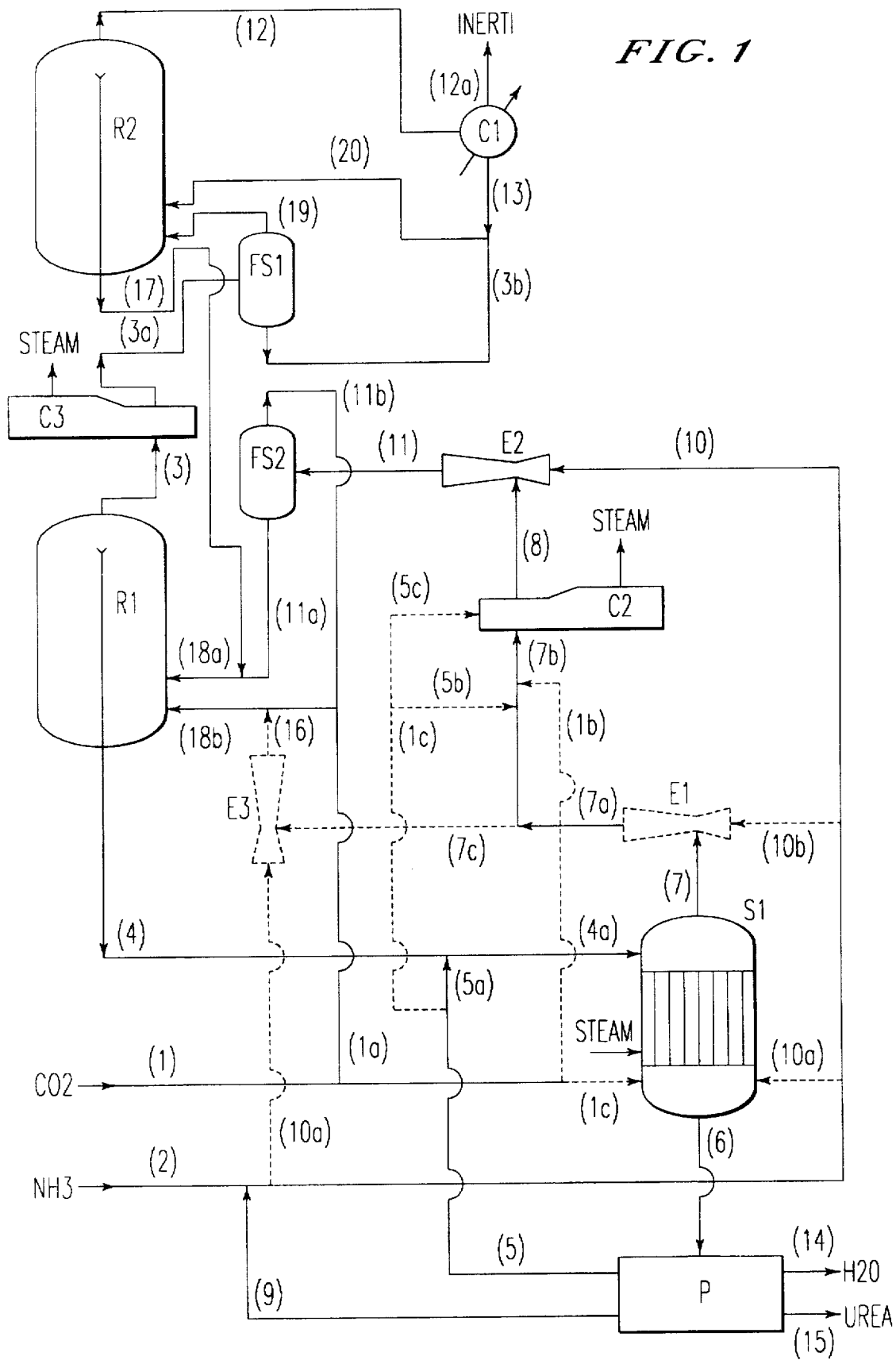
FIGS. 1, 2, 3 and 4 each schematically represent a preferred embodiment of the process of the present invention.

The term "communicating", as used in the present description and in the claims with reference to two different zones or apparatus of the process of the present invention, means that amounts of matter, either continuously or stepwise, are exchanged between each other, either directly through one or more connecting lines, or indirectly through a route comprising connecting lines and other pieces of equipment.

According to the process of the present invention, which is usually carried out in continuous in an appropriate plant, fresh ammonia and carbon dioxide are continuously fed to the plant to balance the corresponding quantity of reagents used up for the formation of the urea obtained at the outlet of the final separation and prilling section of the plant. All the equipment in contact with the corrosive mixtures containing ammonia, water, ammonium carbamate and carbon dioxide, as such or mixed with each other, is generally made of or lined with corrosion-resistant metals or alloys according to the normal construction regulations for this type of plant.

The fresh ammonia and carbon dioxide can be fed directly to the reaction step, but are preferably used, at least in part, as driving fluid in one or more ejectors, to supply the necessary thrust for recirculating fluids like, e.g., the first gaseous stream discharged from the stripping step (c), and/or ammonium carbamate coming from the condensation step (d). Ammonia is particularly preferred to be used for this purpose.

As an alternative, or also contemporaneously with the use in the ejectors, the fresh ammonia or carbon dioxide can be used, either totally or in part, as a stripping fluid in the stripper and/or sent directly to the condenser.

As already specified, reaction step (a) is carried out, according to the present invention, in two distinct zones operating at basically the same pressure of between 90 and 250 ata, preferably between 130 and 180 ata. The term "at basically the same pressure", as used in the present invention and claims, should be intended in the sense that small differences of pressure are allowed, but are however not very significant with respect to the total pressure itself. This comprises, for example, the small differences in pressure that can be made up for by arranging the equipment and zones of interest at different heights, and/or by ejectors.

In the process of the present invention, operating, in reaction step (a), with an excess of ammonia with respect to the stoichiometric ratio with the carbon dioxide necessary for producing ammonium carbamate and, subsequently, urea (2/1 in moles), the stream leaving the first reactor and, in general, most of the liquid streams which are formed in the process, usually contain ammonia in excess. During the present description, reference is made to the composition of these liquid streams and mixtures (or also biphasic) considering, conventionally, that all the carbon dioxide is present in the form of ammonium carbamate, and the remaining excess of ammonia is present as free ammonia in solution or, more simply, as ammonia.

In addition, to simplify the present description, the term "liquid" is used indifferently with reference to streams or mixtures of the process according to the present invention, which consist of either a single liquid phase or a mixed liquid-vapour phase in which the liquid is prevalent (more than 50% by weight).

In the present process, the liquid streams containing ammonium carbamate are preferably all at a temperature which is equal to or more than 130° C.

Finally, according to the present invention, the term "gaseous" is used for those streams or mixtures in which the liquid phase is essentially absent, whereas the term "prevalently gaseous" referring to a reactive mixture or stream should be interpreted in the sense that gas and liquid are still present in equilibrium, but the gas phase is more than 50% by weight, preferably more than 70% by weight, with respect to the total weight (or total mass flow rate, in the normal case of streams in a continuous process) of the mixture of interest.

According to the present process, the first of the two reaction zones previously mentioned operates at temperatures of between 170° and 230° C., preferably between 190° and 210° C. The different streams deriving from the recycled carbamate not transformed into urea and excess ammonia coming from the separation steps situated downstream, the feeding streams of the fresh reagents (the latter possibly premixed with the recycled streams), as well as the further liquid stream coming from the second reaction zone, are preferably fed to this first reaction zone. The molar ratios ammonia/carbon fede in the total feeding are preferably between 2.1 and 6.0, more preferably between 2.5 and 4.5. The conditions in the first reactive zone (or main reactor) give the formation of quite a significant quantity of vapour phase mixed with the liquid phase, the vapour phase being concentrated in the upper part of the reactor, the top prevalently consisting of the gaseous phase which is transferred to the second reaction zone.

Apart from the higher operating temperature, the first reaction zone basically resembles a normal reactor for the synthesis of urea in a traditional process. The reactor is normally equipped with several plates, of a type selected from the various ones known in the art to carry out the optimal flow conditions. The reactor can in turn be subdivided into several reaction zones, suitably connected with one another, preferably in a cascading formation, possibly also having different feeding streams at different heights.

The heat developed and more generally the thermal level of the reactor in the first zone of step (a), can be controlled by acting on the thermal level of the streams of carbon dioxide and/or ammonia fed to the reactor and/or on the basis of the division of these feeding streams between stripper, condenser and reactor and/or on the quantity of heat removed in the condenser.

This first reactor must have a hold-up of liquid which is such as to allow an average residence time of this of between several minutes and tens of minutes, preferably between 5 and 40 minutes, to enable the ammonium carbamate formed by reaction of the ammonia with the carbon dioxide to dehydrate to urea.

The second reaction zone, according to the present invention, operates at a temperature which is lower than the first, usually between 140° and 200° C., preferably between 150° and 185° C., with a temperature difference between the two zones preferably between 5° and 60° C. It is fed with the second prevalently gaseous stream leaving the top of the first zone, which basically comprises ammonia, water, carbon dioxide and possibly inert gases such as nitrogen, argon and small quantities of oxygen introduced to limit corrosion of the plants according to what is known in the art. The possibility of also feeding to the second zone part of the ammonia and carbon dioxide reagents necessary to compensate for those transformed into urea and/or of feeding, either totally or in part, the above first gaseous mixture leaving the stripper of step (c), is not however excluded from the scope of the present invention. The molar ratios ammonia/carbon dioxide in this second reaction zone normally depend on the operating conditions of the reactor in the first reaction zone, which determine the composition of the prevalently gaseous stream fed to the second zone. These molar ratios can however vary within a relatively wide range, depending on the running conditions of the plant, and are preferably, in the overall feeding to the second reactor, between 2.1 and 7.0.

The second reaction zone of step (a) of the present process normally comprises a reactor equipped with the same anti-corrosion expedients mentioned above. This may consist, for example, of a second reactor separate from the first and preceded by a condenser on the feeding line coming from the first reactor, or it may consist in a condenser-heat exchanger with the production of vapour or heating of a different liquid or gaseous stream, which condenser-heat exchanger can also coincide with the same condenser as step (d).

In a particular embodiment of the present invention, the second reactive zone is carried out in an exchanger-dephlegmator situated on the top of the first reactor so as to form, in practice, a single apparatus. This exchanger-dephlegmator is separated from the main reactor, situated below, by an element, consisting for example of a septum or stack plate, equipped with devices suitable for allowing the passage of the vapour phase from the first to the second reactive zone, and collecting the liquid formed in this second zone. The latter is transferred to the underlying main reactor by appropriate recycling lines, and is preferably fed to the lower part thereof According to the process of the present invention, in this second zone ammonium carbamate is formed according to the reaction (1a), favoured by the lower temperature with respect to the first zone, and, possibly, there is also the formation, in part, of urea according to reaction (1b), depending on the operating conditions of the second reactor. There is consequently the formation of a liquid mixture containing ammonium carbamate and residual ammonia deriving from the excess present in the feeding, and preferably also containing urea and the corresponding water formed. This liquid mixture is then transferred and reintroduced to the first reaction zone, preferably being fed to the lower part thereof. It can possibly be combined with the recycled liquid streams coming from the sections downstream of step (a), before being reintroduced.

The use, in the second reaction zone, of a reactor preceded by an exchanger/condenser fed with the prevalently gaseous stream coming from the first reactor, can give rise to the formation of significant quantities of urea (as well as carbamate) in the secondary reactor; the alternative use as secondary reactor of the single condenser situated upstream of the main reactor, or a reactor with a limited residence time and in which there is basically a very rapid reaction, gives rise to a prevalent formation of carbamate: in both cases the liquid mixture leaving reaction step (a) and fed to the stripper consists of a stream with a lower concentration of carbamate owing to the higher thermal level of the main reactor.

According to the present invention, it is critical that a suitable quantity of prevalently gaseous mixture which is formed in the first reaction zone is transferred to the second reaction zone. This transfer can be carried out in various ways depending on the operating conditions of the synthesis cycle and the process scheme. In particular, for example, the gaseous mixture can be already separated in the first zone from the first liquid mixture leaving the reaction step, and sent to the second zone from the head of the first reactor. Or said first liquid mixture and the above prevalently gaseous mixture can be taken as a single biphasic mixture from the first reaction zone, and subsequently separated into two component phases (liquid and gaseous, for example in a suitable phase separator), and transferred respectively to the second reaction zone and the above-mentioned decomposition-stripping step (c). In the latter case, the separation of the two phases can also take place at the inlet of the same decomposition-stripping step, using for example the head of the stripper, to which the biphasic mixture is fed, as phase separator.

In the process of the present invention, a third gaseous stream rich in inert products which must be discharged, can be separated from the head of the second reaction zone. This gaseous stream, before the inert products are discharged, is subjected to condensation, with the possible help of a phase separator, to recover the ammonia and carbon dioxide contained therein, which are recirculated directly to one of the two reaction zones.

In another form of embodiment, this third gaseous stream is subjected to washing in countercurrent with the recycled aqueous stream coming from step (f), thus producing a gaseous phase basically containing inert products which is discharged, and a liquid stream which is fed, as the rule, to the condenser.

In a further form of embodiment, the third gaseous stream is recirculated and fed as a stripping agent to one of the apparatuses necessary for carrying out step (f), such as, for example, the concentration and purification section of urea or a decomposition section of the carbamate at medium or low pressure.

The decomposition-stripping step (c) is normally carried out in a stripper normally heated by indirect vapour at a high pressure. The temperature of the stripper is normally between 160° and 220° C., whereas the pressure is equal to or slightly lower than that of the reactor, in order to enable the recirculation to the latter of the decomposition products (first gaseous stream) by ejectors and/or the different height positioning of the equipment.

Under the above conditions, the ammonium carbamate tends to rapidly decompose forming ammonia and carbon dioxide which are simultaneously removed from the liquid phase by stripping, whereas the urea already formed in the reactor remains basically unaltered. The stripping can be carried out using fresh ammonia or carbon dioxide as transport gas. Various examples of processes for the synthesis of urea using the above principle are described in literature. For example, U.S. Pat. No. 3,356,723 of STAMICARBON, describe the use of carbon dioxide as a stripping gas. On the other hand patent GB 1,016,220 of SNAMPROGETTI describes the use of ammonia for the same purpose.

In a preferred embodiment of the present invention, the decomposition-stripping step is carried out using the same ammonia present in excess in the stream leaving the reactor, as transport gas. Further details on this preferred technology can be found, for example in U.S. Pat No. 3,876,696 of SNAMPROGETTI, whose content is included herein as reference. This latter technology is referred to with the term "autostripping".

According to the present invention, the decomposition-stripping step can also be carried out in two pieces of equipment (strippers) in series, possibly of different types and operating under different conditions from one another, as described, for example, in patent GB 1,581,505, whose content is included herein as reference.

According to the present invention, a first gaseous mixture of ammonia, carbon dioxide and water is obtained from the decomposition and stripping step (c), in which the content of water is normally between 0.0 and 15%, preferably between 0.5 and 10.0% by weight, with respect to the total weight of the gaseous mixture. This water content is about the same as that one normally obtained in stripping operations at a high pressure carried out according to the processes mentioned above.

Step (c) can also be carried out using, as a stripping gas, a suitable quantity of gaseous mixture which is formed in step (a), either in the first or the second reaction zone. For example, the quantity of gaseous mixture which is transferred to step (c) as stripping agent, can be part of the gaseous mixture available from the first reaction zone, the remaining part being transferred independently to the second reaction zone, or said gaseous mixture can be the inert gas-containing gaseous stream taken from the head of the second reaction zone.

According to a particular embodiment of the present invention, all said second prevalently gaseous mixture taken from the first reaction zone is passed through said decomposition-stripping step before being fed to the second reaction zone. Preferably, in this case, the second reaction zone coincides with the condenser of condensation step (d). The gaseous mixture from the first reaction zone, and the gases formed during the decomposition-stripping step are mixed and fed together to the condenser-second reactor. Surprisingly, by carrying out the process of the present invention according to this particular embodiment, a further advantage is achieved, besides an enhanced conversion of the reactants, i.e., an improved efficiency of the decomposition-stripping step, whereby the second liquid mixture leaving the bottom of the stripper contains a lower amount, preferably less then 5% by weight, of unreacted ammonium carbamate. Consequently, the separation step (f) is much less onerous in terms of operating costs and investment than the corresponding step in traditional processes, and, furthermore, less water is needed to recycle the carbamate to the reaction step.

The decomposition-stripping step (c) is generally carried out in pipe bundle equipment with a liquid film drop. Preferably, the mixture leaving the reactor, together with at least part of the fourth liquid mixture coming from the steps downstream of the stripper, is fed to the head of the equipment and forms a film drop on the walls of the pipe bundle. Other known equipments suitable for the purpose can also be used in the process of the present invention The condensation step (d) of the present process is normally carried out in suitable condensers, for example pipe bundle condensers, in which the condensation heat is used to heat the other fluids. The condensation heat is preferably used for the production of steam, but can also be used to supply heat directly to one of the subsequent decomposition steps of the ammonium carbamate at medium or low pressure. The condensation step can be carried out under the usual conditions (temperature, pressure and composition) used in the known processes, provided that they are such as to prevent the formation of solid crustes or deposits of ammonium carbamate in the condenser and/or lines leaving the condenser. The condensation is generally carried out at temperatures higher than 140° C., preferably between 150° and 180° C., at pressures slightly lower than those of the reactor.

According to an embodiment of the present invention, not all the first gaseous mixture coming from the stripping (c) is sent to the condenser (d), but a part, preferably from 5 to 50% by weight, is sent instead as such to the reaction step (preferably to the first zone operating at a higher temperature) in order to favour the enthalpic control of the reactor.

The transfer to reaction step (a) of the third liquid mixture leaving the condenser in step (d) and, where desirable, of part of the non-condensed gaseous mixture leaving the stripper, is normally carried out, in step (e), by ejectors or fall (of the liquid mixture). The differences in pressure to be compensated for the circulation of the streams of interest are sufficiently small as to not necessitate mechanical thrust devices. The ejectors preferably use ammonia as driving fluid. The above mixtures are preferably transferred to the first reaction zone of step (a).

The separation of urea from ammonia and ammonium carbamate still present in the second liquid stream leaving the decomposition-stripping step is carried out, according to step (f) of the present process, in subsequent decomposition (of the ammonium carbamate) and separation sections, operating at medium (from 15 to 25 ata) and/or low (from 3 to 8 ata) pressure. For the purposes of the present invention, this separation step (f) can be carried out by any of the methods described in the specific literature of the field, allowing a recycling liquid stream to be obtained, containing an aqueous solution of ammonium carbamate and ammonia, and, possibly, also a stream basically consisting of ammonia, which is normally recompressed and joined to the fresh feeding ammonia stream.

Decomposition, separation and purification sections suitable for the purposes of the present invention are, for example, those schematically represented in FIGS. 1 to 5 of the publication "Encyclopedia of Chemical Technology" mentioned above.

The urea separated from substantially all the residual ammonium carbamate and ammonia in the decomposition and stripping steps at medium and low pressure, is then subjected to a final dehydration step under vacuum (up to 0.1 ata) which removes the water and completes the separation of the carbamate, obtaining, on the one hand, waste water and, on the other, basically pure urea sent to the usual prilling processes, etc. The waste water thus produced, after separation and recycling of the last impurities of $NH_3$ and $CO_2$, is discharged from the plant.

According to a preferred embodiment of the present invention, the different streams containing ammonium carbamate (and/or other composite forms of carbon dioxide) coming from different sub-sections of step (f) (decomposition of the carbamate at medium and low pressure, recondensation of the carbamate, dehydration of the urea, purification of the waste products) are joined together in the above recycling stream, which, after recompression, is then fed, either totally or in part, to condensation step (d), which can also coincide with the second reaction zone, as mentioned above. The coincidence between the condensation step (d) and the second zone of reaction step (a), obviously refers to the physical coincidence of the equipment destined for the purpose, the meaning and effects of the two steps remaining, from a technical point of view, quite different.

In a preferred embodiment of the present invention, from 50 to 100% by weight of said recycled liquid mixture is fed to decomposition-stripping step (c) together with the first liquid mixture coming from the first reaction zone. In this way there is a substantial reduction in the quantity of water present in the reaction mixture with a further increase in the conversion by passage.

According to certain forms of embodiment of the separation and purification of the urea, still included within the scope of the present invention, the recycled ammonia and carbon dioxide can be present as ammonium carbonate, bicarbonate or carbamate, or a mixture thereof, depending on the temperature and pressure of the mixture.

The process according to the present invention allows a significant increase of the conversion by passage of carbon dioxide into urea, which can reach, under optimum conditions, values of between 70 and 85%. This is surprisingly achieved without operating at extremely high pressures, but with the simple expedient of carrying out the reaction in two distinct and intercommunicating zones, operating at different temperatures but at basically the same pressure. A further advantage of the present process consists in a lesser consumption of vapour in the stripping operation at high pressure (step (c)), owing to the smaller quantity of carbamate with respect to the urea in the first liquid mixture leaving the reaction step.

Furthermore, the present process has the advantage of being able to be easily and surprisingly carried out with a few simple modifications of a traditional, pre-existing plant.

A further object of the present invention therefore relates to a method for improving an existing process for the production of urea starting from ammonia and carbon dioxide with the intermediate formation of ammonium carbamate, which operates with a synthesis section at high pressure comprising:

a first synthesis reactor of urea operating with an excess of ammonia at pressures of between 90 and 250 ata, with the formation of an outgoing liquid stream containing urea, water, ammonia and ammonium carbamate;

a decomposition step of the ammonium carbamate in said liquid stream and separation step (with stripping) of a gas stream containing carbon dioxide and ammonia thus formed, situated downstream to said reactor, and a condenser of the gas stream leaving said decomposition-stripping step, with the formation of a liquid stream containing ammonium carbamate fed, as a recycled product, to said first reactor, characterized in that it comprises the following operations:

(i) setting up a second reactor for the formation of ammonium carbamate and, possibly, urea starting from carbon dioxide and ammonia in excess, operating basically at the same pressure as the above first reactor, preferably at temperatures of between 140° and 200° C., more preferably of between 140° and 185° C., and this second reactor may also coincide with the above existing carbamate condenser;

(ii) setting up suitable elements and connection lines for transfer of material from the top of the above first reactor to the second reactor, and the corresponding transfer of material from the second reactor to the first;

(iii) establishing the operating conditions of said first and second reactors so that the temperature of the second reactor is lower, preferably from 5° to 60° C. lower, than the temperature of the first, with the formation, in the latter, of a vapour phase mixed with the liquid phase;

(iv) transferring, from the top of the first reactor to the second, a gas or prevalently gas stream containing carbon dioxide and ammonia, in a quantity of at least 5% by weight, preferably in a quantity equal to or higher than 10% by weight, more preferably in a quantity of between 20 and 40% by weight, with respect to the weight of the above liquid stream leaving the first reactor, with the subsequent formation, in the second reactor, of a liquid mixture containing ammonium carbamate and, preferably also urea, which is transferred to the first reactor, feeding it preferably from below.

The above method for improving an existing process for the production of urea (also identified with the English term "retrofitting", commonly used in the specific reference field) in practice results in a process comprising two distinct reaction zones, basically analogous to the process of the present invention. Consequently all the different forms of embodiment, and preferred conditions previously specified, should be considered valid as a description of the above "retrofitting" method.

The improved process according to the present invention is further illustrated by the four figures enclosed herewith, wherein:

FIG. 1 schematically represents a preferred embodiment of the process of the present invention, wherein the reaction step is carried out in two separate reactors, interconnected with one another by elements for the exchange of matter.

Figure 2:
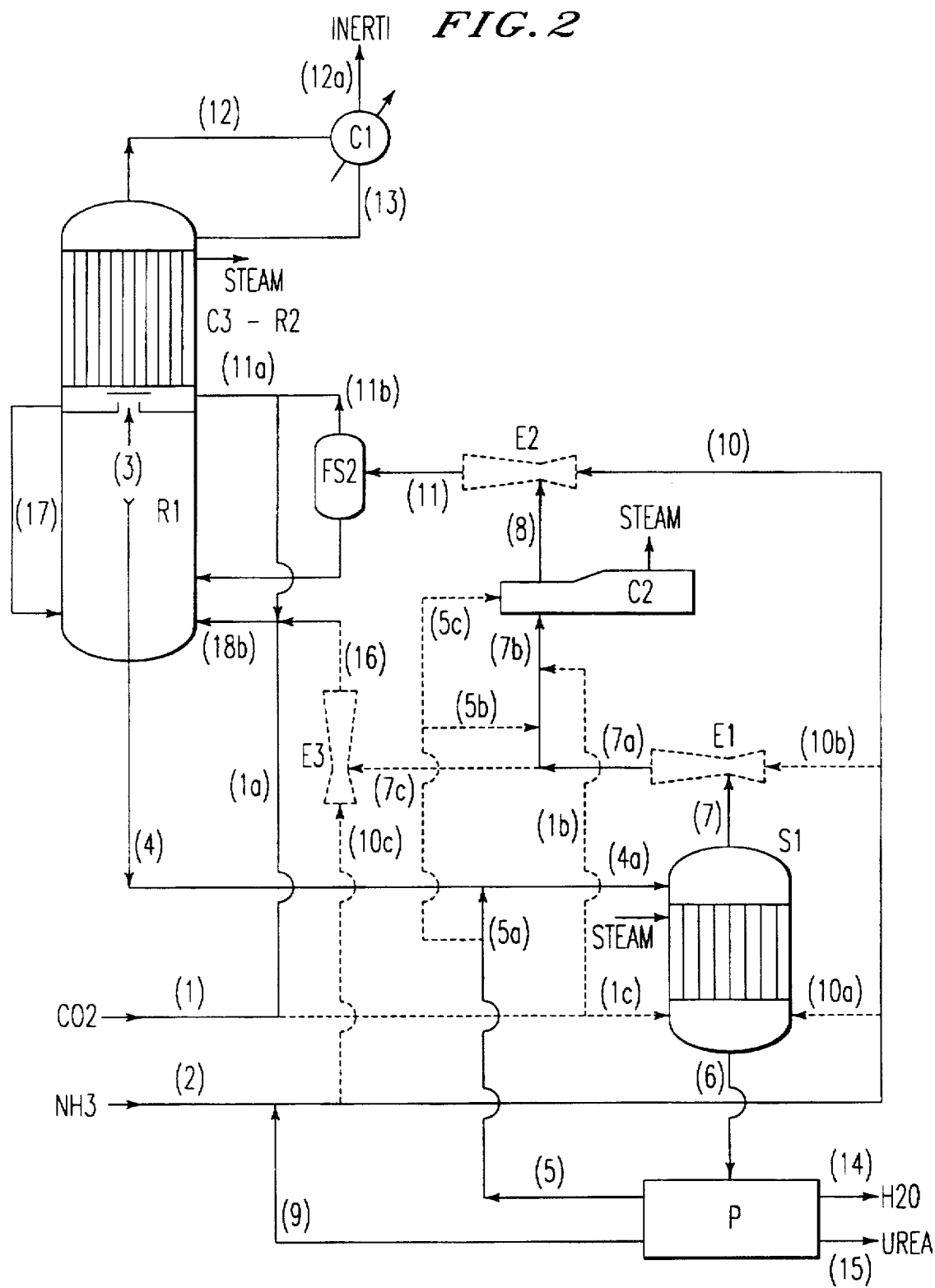

FIG. 2 schematically represents a preferred embodiment of the process of the present invention, wherein the reaction step is carried out in a single apparatus subdivided into two zones communicating with each other for the exchange of matter.

Figure 3:
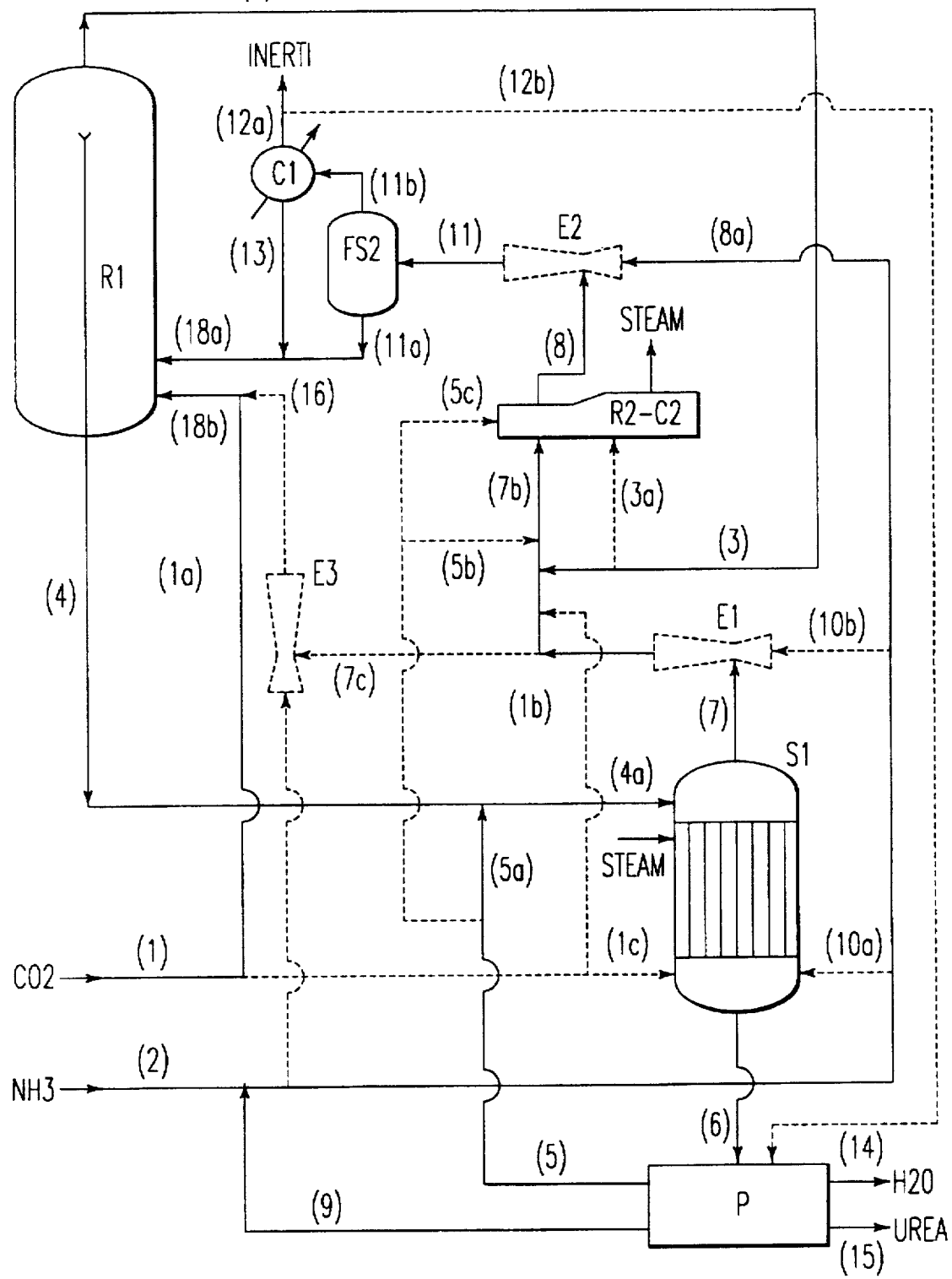
Figure 4:
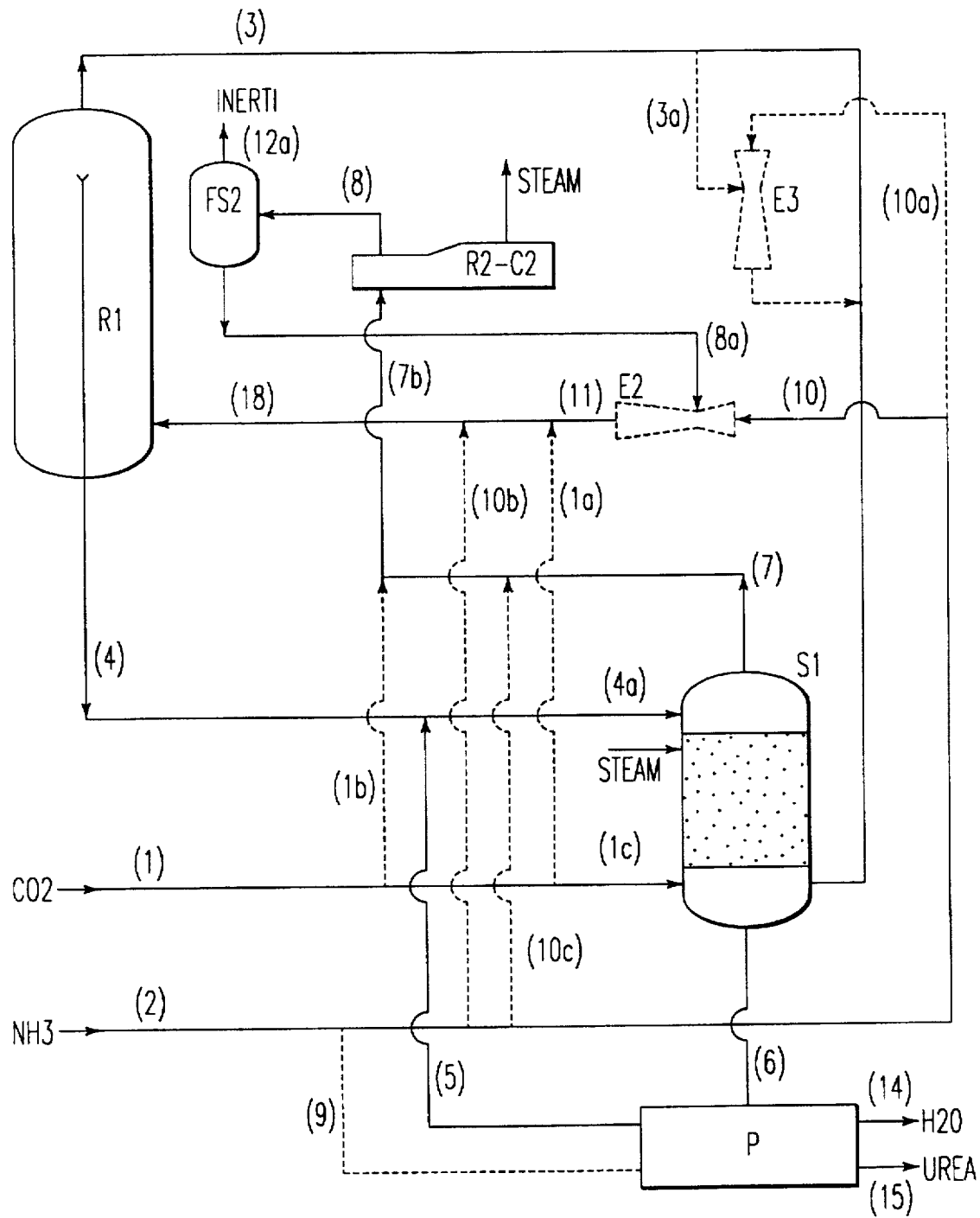

FIG. 3 schematically represents a preferred embodiment of the process of the present invention, wherein the reaction step is carried out in two reactors, one of which is also the condenser of the gases leaving the stripper at high pressure;

FIG. 4 schematically represents a preferred embodiment of the process of the present invention, which is substantially similar to the process according to previous FIG. 3, except for the fact that gases leaving the first (main) reactor are passed through the stripper at high pressure before entering the second reactor, instead of being fed directly to the same.

In the above figures, the dashed lines represent alternative possibilities, not mutually exclusive, for the embodiment of the process of the present invention. Functional details such as pumps, valves and other apparatuses which are not significant for fully understanding the processes sketched are not shown in the above figures. The selection of the type and position of such pieces of equipment, which are used in the practical embodiment of a plant for the production of urea according to the present invention, is indeed based on the usual designing criteria of a traditional plant and is well within the skills of a medium expert of the art. The process of the present invention should in no case be considered as being limited to what is shown and described in the enclosed figures, which hold an illustrative function only.

The diagram of FIG. 1 shows reactor R1 which is connected, by means of an overflow and line 4, to the stripper S1. The latter is connected from below to the separation and purification section of urea P, from which line 5 leaves, for the recycling of the carbamate. Line 5 can in turn be directly connected to the condenser C2 through line 5c, or indirectly through line 5b, or can join line 4, by means of line 5a. Several contemporaneous connections are also possible, with partialization of the stream of line 5. Lines 15, of purified urea, and 14 of waste water also leave the same section P. The stripper S1 is connected from above to the condenser C2 by means of line 7, together with the ejector E1 (driven by the stream of ammonia coming from line 10b) and lines 7a and 7b. The stripper S1 can also be directly connected to the reactor R1 (with partialization of the gaseous stream 7) by means of lines 7a, 7c and 16, among which the ejector E3, driven by the stream of ammonia coming from line 10c, is possibly placed. The outlet of the condenser is represented by line 8, followed by line 11, between which the ejector E2 is possibly placed, which is also joined to line 10 which carries fresh (line 2) and recycled (line 9) ammonia, the latter coming from section P for the separation and purification of the urea. Line 11 is connected to a phase separator FS2, from which the gaseous line 11b leaves from above, and the liquid line 11a leaves from below. Line 1 of fresh carbon dioxide can directly feed the reactor (line 1a) after receiving line 11b coming from the separator FS2, or it can be connected to the condenser (line 1b) or to the bottom of the stripper (line 1c), or also to more than one of these devices, with partialization. Line 11a joins line 17 coming from the second reactor R2, to form liquid feeding line 18a of the reactor R1. Gaseous feeding line 18b of the reactor collects (possible) streams 1a, 11b and 16.

Line 3 leaving the top of the reactor R1 is connected to the condenser C3 and subsequently (line 3a) to the phase separator FS1, from which the reactor R2 is fed by means of lines 19 (gas) and 3b (liquid). Line 17 leaves the reactor R2 through an overflow, and returns to the first reactor R1 after joining the recycled liquid streams to form line 18a. Line 12 leaves the top of the reactor R2 and is connected to the condenser C1, which waste out the inert products through line 12a and allows the recycling of the condensates through line 13 which joins the above line 3b coming from the separator FS1, to form line 20 feeding liquid to the reactor R2.

The diagram in FIG. 2 basically shows the same elements, with the same meaning, as the diagram in FIG. 1, as far as the reactor R1 is concerned and the sections downstream of this (stripper, recycling of the carbamate and purification of the urea). In this case however, the reactor R1 is structured to be directly connected to a dephlagmator C3-R2 in the upper part, forming with this a single piece of equipment. The dephlagmator has the contemporaneous function of condenser C3 and second reactor R2, and communicates with R1 through the opening 3 inserted in a stack-plate (to collect the condensed liquid), which is in turn connected to R1 by means of returning line 17, which basically has the same meaning as line 17 in the previous FIG. 1, but which is not joined, in this case, to the recycled liquid line 11a. In this case therefore, the reactor R1 receives the two lines 17 and 11a separately; although the case wherein these lines join to form a single line for liquid feeding, analogous to line 18a in FIG. 1, is obviously also included in the scope of the invention.

The dephlagmator C3-R2 can possibly also receive, through line 11c, a part of the gaseous stream coming from the phase separator FS2.

Line 12 leaves the top of the dephlagmator C3-R2 and is connected to the condenser C1, which liberates the inert products through line 12a and allows the condensates to be recycled through line 13 which is directly connected to the upper part of the dephlagmator C3-R2.

The diagram of FIG. 3 refers to a particular practical embodiment of the present invention, wherein the second reactor consists of the same condenser of the gases coming from the stripper at high pressure. This diagram shows the reactor R1 which is connected, from the top to the condenser-reactor R2-C2 through line 3, and from the bottom, through an overflow and line 4, to the stripper S1. The latter is connected from below to the separation and purification section of urea P, from which line 5 leaves for the recycling of the carbamate. Line 5 may in turn be directly connected to the condenser-reactor R2-C2 through line 5c, or indirectly through line 5b, or it may join line 4, by means of line 5a. Several contemporaneous connections are also possible, with partialization of the stream of line 5. Lines 15, of purified urea, and 14 of waste water also leave the same section P. Through line 7, the ejector E1 (driven by the stream of ammonia coming from line 10b) and lines 7a and 7b, the stripper S1 is connected from the top to the condenser-reactor R2-C2. Line 7b is the result of the union of line 7a, of line 3 coming from the top of the reactor R1, and possibly lines 1b and 5b respectively carrying fresh carbon dioxide and the recycled carbamate from the sections at medium or low pressure (section P). The condenser-reactor R2-C2 may also be directly connected to the reactor R1 by means of lines 3–3a.

The stripper S1 may also be directly connected to the reactor R1 (with partialization of the gaseous stream 7) by means of lines 7c and 16, between which there is possibly the ejector E3, driven by the stream of ammonia coming from line 10c. The outlet of the condenser-reactor R2-C2 is represented by line 8, followed by line 11, between which there is possibly the ejector E2 which is also reached by line 10 which carries fresh ammonia (line 2) and the ammonia from recycling (line 9) coming from section P for the separation and purification of urea. Line 11 is connected to a phase separator FS2, from which the gaseous line 11b (containing possible inert products) leaves from the top connected to the condenser-separator C1, and the liquid line 11a from the bottom, which joins line 13 coming from the separator of the inert products C1 to form line 18a carying the liquid feeding to the reactor R1. A gaseous mixture (stream) which forms the blowdown of the inert products is removed by means of line 12a. Alternatively, this gaseous mixture is sent, by means of line 12b, to one of the decomposition steps of the residual carbamate in section P, where it acts as stripping agent (according to a known technology of SNAMPROGETTI). The inert products are then discharged directly from section P itself.

Line 1 of fresh carbon dioxide may directly feed the reactor (line 1a) or may be connected to the condenser (line 1b) or to the bottom of the stripper (line 1c) or also to more than one of these devices, with partialization.

The diagram of FIG. 4 comprises the reactor R1 which is connected, from the top, through line 3, to the lower portion of stripper S1, and, from the bottom, through an overflow and line 4, to the upper portion of the same stripper S1. This is connected from below to the separation and purification section of urea P, from which line 5 leaves for the recycling of the carbamate, which, in this embodiment, is fed back to the stripper by joining line 5 to line 4. Lines 15, of purified urea, and 14 of waste water also leave the same section P. Through lines 7 and 7b, the stripper S1 is connected from the top to the condenser-reactor R2-C2. Line 7b is the result of the union of line 7 and, eventually, lines 1b and/or 10c, carrying respectively fresh carbon dioxide and pure ammonia (fresh plus recycled). Line 3, connecting R1 and S1, may also include (line 3a) an ejector E3 driven by an ammonia stream fed through line 10a.

The outlet of the condenser-reactor R2-C2 is represented by line 8, which is connected to a phase separator FS2, from which the gaseous line 12a leaves from the top, carrying possible inert products. The liquid line 8a leaves from the bottom of FS2 toward the reactor R1, eventually passing through an ejector E2 driven by ammonia through line 10. The liquid feeding line 18, of the reactor R1, is the result of lines 11, exiting the ejector E2, and possible lines 1a and 10b, carrying respectively fresh carbon dioxide and pure ammonia.

With reference to the above FIGS. 1, 2, 3 and 4 several embodiments of the process of the present invention are described, said description being intended not to limit by any way the overall scope of the invention itself.

With reference to the scheme of FIG. 1, fresh ammonia, compressed at 160–200 ata and fed through line 2, is merged with the recovered ammonia (line 9) coming from section P, and the resulting stream is sent partly to the ejector E2, through line 10, and partly to ejector E1 (line 10b) where it acts as driving fluid of the gases coming from the stripper S1 through line 7. Alternatively, depending on the necessities, the ammonia can be fed, either totally or in part, to the stripper S1 through line 10a, in which case line 10b (and consequently the ejector E1) may be absent. This is the case of stripping carried out with ammonia.

The gas stream 7a leaving the ejector E1 (or the stripper if E1 is absent), to which possibly either a part, or even all of the fresh carbon dioxide fed to the plant is added by means of line 1b, is fed to the condenser C2 (line 7b).

Alternatively, the stream 7a can be partialized and 50–70% fed to the condenser C2 (line 7b), together with the possible fresh carbon dioxide, and the remaining part (line 7c) fed to the reactor R1, possibly through the ejector E3, still using ammonia as driving fluid (line 10c).

In this way, the enthalpic balance is controlled in the reactor R1, which operates at relatively high temperatures (190°–210° C.) and pressures of between 140–160 ata, and requires, preferably, a part of the feeding to be carried out with recycled gaseous streams having a higher enthalpic content and/or containing a greater quantity of free $CO_2$ capable of forming ammonium carbamate.

Preferably, up to 30% of the ammonia coming from lines 2 and 9 is fed to the ejector E1, via 10b, from 50 to 90% is fed to the ejector E2, via 10, and the remaining part to the ejector E3 via 10c. Under the normal operating conditions of the process of the present invention the above streams 10, 10b and 10c contain ammonia prevalently in its liquid state.

The fresh $CO_2$ (line 1) can be analogously sent by means of lines 1a and/or 1b depending on the enthalpic necessities of the reactor R1, but also via line 1c to the stripper S1, in which case it is also used as a stripping agent. Most of the fresh carbon dioxide, after compression, is preferably sent to the reactor (60–80%) (line 1a) and part of it is fed to the condenser C2 (line 1b).

The ammonia and carbon dioxide contained in the feeding streams 7b and (possibly) 5c react in the condenser C2 (basically consisting of a heat exchanger of suitable shape and sizes), at a pressure which is similar to or slightly lower than that of the reactor and at the highest temperature, preferably between 150° and 185° C., which is suitable in order to obtain a liquid stream (third liquid mixture) prevalently containing ammonium carbamate and ammonia, and lesser quantities of water and, possibly urea. The latter may already be formed in small quantities during this condensation step, as the operating conditions are already suitable for partially moving the chemical equilibrium (1b) previously mentioned to the right. The condensation, which is exothermic, is used for the production of vapour or for heating streams at low or medium pressure of the subsequent purification section of urea. The liquid stream produced in the condenser is fed to the reactor via lines 8 and 11, between which the ejector E2 is preferably situated.

The stream 11, generally consists of a mixed gas-liquid phase with a prevalence of the latter, and is preferably separated into the two phases in the separator FS2, from which the gaseous stream 11b and the liquid stream 11a leave, this latter being joined to stream 17 before feeding the reactor R1.

The overall feeding of the reactor consists of the liquid stream 18a (comprising the stream 17, coming from R2) and the gaseous stream 18b.

The reactor R1 can be of the type used in the traditional processes, but is preferably modified to facilitate the flow and exchange between the liquid and gaseous phase which in this case is considerable. R1 is generally considered the main reactor as it involves streams and volumes which are usually two or three times those of R2. The different streams and enthalpic balance of the reactor are preferably selected to enable a significant quantity of vapour phase to be progressively formed towards its head. This can be obtained by selecting the parameters on the basis of the equilibrium data available and, possibly, by empirically adjusting these, according to the usual techniques known to the expert.

The liquid stream discharged from the reactor R1 by means of the overflow T and line 4, containing urea, water, ammonia and ammonium carbamate, is fed to the stripper S1 for separation of part of the carbamate not converted into urea according to the normal technologies used in the traditional plants.

In a preferred embodiment, the stream of line 4 is joined to line 5a containing a part, (preferably from 60 to 90%) of the recovered aqueous stream, comining, via line 5, from section P for the separation and purification of urea, and is fed (line 4a) to the stripper. The possible remaining part of this recovered stream is sent to the condenser C2, directly via line 5c, or indirectly via line 5b.

In a particular embodiment of the present invention, the feeding 4a to the stripper S1 is partialized at different heights of the stripper itself From the top of the reactor R1 a gaseous stream, preferably corresponding to 20–40% by weight with respect to the effluent of line 4, containing ammonia, water and carbon dioxide, is fed to the condenser C3 where the partial condensation takes place of a liquid phase containing ammonium carbamate and water. The semiliquid mixture is separated into the gaseous and liquid components in the phase separator FS1, both fed to the secondary reactor R2, which operates adiabatically at temperatures of between 170° and 185° C., with residence times preferably of between 5 and 35 minutes. Under these conditions, in the reactor R2 there is the formation of ammonium carbamate which further reacts to give significant quantities of urea, up to 70% conversion, with respect to the quantity of $CO_2$ in the gaseous stream coming from R1.

The gaseous stream 7 discharged from the head of the stripper, containing $NH_3$ and $CO_2$ and having a low water content, preferably less than 10% by weight and, more preferably less than 5% by weight, is sent to the condenser C2 (lines 7a and 7b) through the ejector E1, using $NH_3$ as motor fluid. The stream 6 discharged from the bottom of the stripper S1, containing all the urea produced, is sent to the subsequent purification and concentration steps, which are schematically joined together in section P in the scheme of FIG. 1. The streams of $NH_3$ and recovered carbamate, already mentioned above, come from this section and pure urea is discharged through line 15 together with water through line 14.

A particular embodiment of the process of the present invention is represented by the scheme of FIG. 2, wherein the two reaction zones are included in a single apparatus C3-R2 divided into two intercommunicating sections, rather than being situated in two physically separated reactors. The process of the present invention can be carried out in the plant sketched in FIG. 2, basically with the same preferred characteristics and conditions already described in the plant scheme of FIG. 1 (to which reference is made), except for the condenser-dephlagmator C3-R2.

The use of a "dephlagmator" as heat exchanger in the second reaction zone at a lower temperature can have various interesting advantages. In fact a dephlagmator allows the physical, continuous removal of products formed therein from the reagent products coming from R1: in this specific case carbamate and, possibly urea in the liquid state (in a ratio which obviously depends on the operating conditions of the apparatus itself) from $NH_3$ and $CO_2$, in the gaseous state, thus making it possible:

to favourably move the chemical equilibrium of the reactions taking place to increase the formation rate of these products The dephlagmator is preferably inserted directly onto the head of the main reactor, separated from this by a stack-plate which collects the liquid condensed by the dephlagmator, this liquid then being sent to the main reactor, and preferably fed at the base. The dephlagmator typically consists of a partial exchanger-condenser, which uses a pipe bundle vertically situated to favour the discharge of the liquid phase formed during the operation. It preferably operates at temperatures of between 150° and 170° C., with relatively rapid contact times, normally of less than 10 minutes, preferably between 0.2 and 5 minutes.

Alternatively, aside of the diagram of FIG. 2, the dephlagmator can also be fed with part of the $CO_2$ and/or fresh or recycled $NH_3$.

With reference to the scheme of FIG. 3, a process for the synthesis of urea according to the present invention is carried out with the main reactor R1 and the stripper S1 basically operating under the same conditions previously specified with reference to the scheme of FIG. 1. In this case, however, the process design is considerably simplified and advantageous, owing to the lower investment costs necessary for its embodiment, as the same exchanger-condenser normally used for the condensation of the gases coming from the stripper, can be fed with the prevalently gaseous mixture separated from the main reactor. In this way, a reactor-condenser R2-C2 is obtained, which has the function of second reaction zone of the present process, contemporaneously maintaining however the function of condensation step (d) of the gases coming from the stripper. The preferred operating conditions of the reactor-condenser R2-C2 are temperatures of between 150° and 170° C., at a pressure basically equal to or slightly lower than that of the reactor R1, with limited contact times, normally of less than 10 minutes, and preferably of between 0.2 and 5 minutes.

Reference is now made to the scheme of FIG. 4 for illustrating a further embodiment of the present invention. The liquid mixture rich in urea leaving the reactor R1 through the overflow and line 4 from the bottom, is sent into the stripper S1, where steam at high pressure is supplied for heating. The gaseous stream 7, basically containing ammonia and carbon dioxide discharged from the stripper S1, is condensed in reactor-condenser R2-C2 (which operates at temperatures of between 150° and 170° C. and at a pressure basically equal to or slightly lower than that of the reactor R1, generating low pressure steam in the heat-exchanger)

and sent to the phase separator FS2, which may also be cooled by external water. The gaseous stream 12a, containing the inert products, is separated and discharged or sent to a further step (not shown in the figure) for the recovery of the ammonia and carbon dioxide contained therein, leaving a carbamate-rich phase exiting from the bottom of FS2 through line 8a. Stream 8a may be recycled to the reactor by gravity, or, possibly, by means of the ejector E2, driven by a feeding gas, preferably ammonia from line 10. Line 11, exiting the ejector, collects fresh carbon dioxide from line 1a and, eventually, more ammonia from line 10b, thus forming the feeding line 18 to the reactor R1.

From the head of the reactor R1, which operates at relatively high temperature (190°–210° C.) and pressures of between 140–160 ata, with formation of a biphasic reactive mixture, the gaseous stream 3 is discharged, basically containing ammonia, carbon dioxide and minor amounts of water, preferably in a total amount of from 20 to 40% by weight with respect to the weight of the liquid stream 4. Stream 3, eventually through the ejector E3, is sent to the lower part of the stripper S1, wherein it is used as a stripping fluid in countercurrent to the liquid stream 4. Surprisingly, this increases the efficiency of the decomposition-stripping step (c) and reduces to almost zero the carbamate in the urea-containing liquid stream 6 discharged from the stripper and sent to the section P of purification and concentration of urea. Fresh carbon dioxide may also be supplied, where advantageous, to the stripper through stream 1c.

The acqueous mixture 5, recovered from the treatment(s) in section P, is normally of relatively low amount, according to this particular embodiment of the invention and is conveniently recycled completely to the stripper S1 together with stream 4 exiting reactor R1.

Some practical examples of embodiment which, however do not limit the overall scope of the claims, provide a better illustration of the aims and advantages of the present invention.

In the following examples, the compositions of the various streams are given with reference to the basic components urea, water, ammonia and carbon dioxide, the latter also comprising the carbon dioxide and ammonia present in the liquid streams in the form of ammonium carbamate, carbonate or bicarbonate.

EXAMPLE 1

A process for the synthesis of urea according to the present invention operates with autostripping in step (c) and comprises two distinct reaction zones corresponding to two separate reactors. Reference is made to the diagram shown in FIG. 1.

735 kg/h of fresh $CO_2$ and 605 kg/h of fresh $NH_3$, containing a total of 13 kg/h of inert products, are fed respectively from lines 1b and 10b to the condenser C2, operating at 150 ata and about 155° C. The gaseous stream coming from the stripper S1 is fed to C2 via line 7. In all, the stream 7b at the inlet of C2 consists of:

$NH_3$=1066 kg/h
$CO_2$=902 kg/h
$H_2O$ =40 kg/h
Inert products=13 kg/h
Total=2021 kg/h The effluent 8 from C2 is sent (via the intermediate ejector E2) to the phase separator FS2 where the gaseous stream 11b and the liquid stream 11a are separated and fed separately to the main reactor (primary) R1 by means of lies 18a and 18b.

The liquid stream 4 discharged from the overflow of the reactor R1 at a temperature of 199° C. (operating temperature of the reactor), contains all the urea produced and is characterized in particular by:

Urea=1000 kg/h
$H_2O$=339 kg/h
$CO_2$=167 kg/h
$NH_3$=461 kg/h Total=1967 kg/h

Under the above conditions, the mixture in the reactor R1 comprises a considerable vapour phase which produces the gaseous stream 3 effluent from R1, consisting of:

$NH_3$=376 kg/h
$CO_2$=212 kg/h
$H_2O$=52 kg/h
Inert products=13 kg/h
Total=653 kg/h This stream is sent to the exchanger-condenser C3 and then, via FS1 and lines 19 and 3b–20, to the secondary reactor R2 operating at about 152 ata and 181° C. (difference with R1=18° C.), where a mixture containing ammonium carbonate and urea is produced.

A liquid stream 17 is discharged from R2, by means of an overflow, consisting of:

$NH_3$=219 kg/h
$CO_2$=60 kg/h
$H_2O$=113 kg/h
Urea=207 kg/h
Total=599 kg/h

From the top of the reactor R2 a gaseous stream 12 is discharged, containing all the inert products which are flushed (line 12a) after passing through the condenser C1. The condensed part is recirculated to R2 by means of line 13. These streams have the following composition, in kg/h:

| stream | 12 | 12a | 13 |
|---|---|---|---|
| $NH_3$ | 56 | 40 | 16 |
| $CO_2$ | 3 | — | 3 |
| $H_2O$ | 5 | 1 | 4 |
| Inert products | 13 | 13 | — |
| Total | 77 | 54 | 23 |

Stream 6 rich in urea leaving the bottom of the stripper S1 (at a temperature of 205° C.) is sent to the subsequent section P for the purification and concentration of the urea, this basically consisting, in this particular case, of typical separation sections at medium and low pressure, and the concentration section which characterizes the traditional SNAMPROGETTI Urea Process of which the general outline is provided, for example, on page 561 of the publication "Encyclopedia of Chemical Technology", previously mentioned. Stream 6 consists of:

$NH_3$=250 kg/h
$CO_2$=75 kg/h
$H_2O$=449 kg/h
Urea=1000 kg/h
Total=1774 kg/h

From the purification and concentration section P, an aqueous stream 5 is recovered, rich in carbamate and consisting in particular of:

$H_2O$=150 kg/h
$CO_2$=75 kg/h
$NH_3$=100 kg/h
Total=325 kg/h which is all sent again to the stripper S1 through line 5a which is joined to the stream 4 leaving the reactor.

A stream of 150 kg/h of $NH_3$ as such is recovered contemporaneously from the same section P through line 9, which is sent (line 10), as motor fluid for the sector E2, to the condenser C2.

The process for the synthesis of urea described above is characterized by a conversion of $CO_2$ to urea, i.e. a molar ratio (urea produced)/(total $CO_2$ fed), equal to 0.82. The liquid stream discharged from the reactor R1 and sent to the stripper is characterized by a molar ratio Urea/$CO_2$=4.8; this ratio is surprisingly higher than that normally obtained for an analogous stream in a traditional plant, having a value of about 1.6.

EXAMPLE 2

A process for the synthesis of urea according to the present invention operates in such a way that the formation reaction of urea basically takes place in a single apparatus comprising the main reactor and a condenser-dephlagmator, communicating with each other, but separated by a stack-plate. Fresh ammonia is used as stripping gas in step (c). Reference is made to the diagram shown in FIG. 2.

A stream of 743 kg/h of fresh $CO_2$ is fed from line 1b to the condenser C2, operating at 150 ata and about 164° C.

A stream of 631 gk/h of fresh $NH_3$ is fed from line 10a to the stripper S1, operating at 150 ata and about 205° C. at the bottom.

Lines 1b and 10a also carry a total of 13 kg/h of inert products.

In all, stream 7b at the inlet of C2 consists of:

$NH_3$=1088 kg/h $CO_1$=904 kg/h $H_2O$=41 kg/h

Inert products=13 kg/h

Total=2046 kg/h

The effluent 8, having the same total flow rate, is sent directly to the main reactor (primary) R1 without passing through any further ejectors or phase separators.

The liquid stream 4 discharged from the overflow of the reactor R1 at a temperature of 198° C. (operating temperature of the reactor), contains all the urea produced and is characterized in particular by:

Urea=1000 kg/h $H_2O$=337 kg/h $CO_2$=168 kg/h $NH_3$=468 kg/h

Total=1973 kg/h

Under the above conditions, the mixture in the reactor R1 comprises a considerable vapour phase which produces the gaseous stream 3 effluent from R1 via the stack-plate, which forms the feeding of the condenser-dephlagmator C3-R2 and consists of:

$NH_3$=349 kg/h $CO_2$=166 kg/h $H_2O$=48 kg/h

Inert products=13 kg/h

Total=576 kg/h

The condenser-dephlagmator C3-R2 operates at 155° C. with the contemporaneous production of carbamate and recovery of vapour. On the bottom of the stack-plate a mixture is collected having the following composition:

$NH_3$=307 kg/h $CO_2$=166 kg/h $H_2O$=47 kg/h

Total=520

A gaseous stream containing all the inert products leaves the top of C3-R2, via line 12, which are flushed (line 12a), together with a small quantity of $NH_3$, after passing through the condenser C1. The condensed part is recirculated to R2 by means of line 13.

Stream 6 rich in urea leaving the bottom of the stripper S1 (at a temperature of 205° C.) is sent to the subsequent section P for the purification and concentration of the urea.

This stream 6 consists of:

$NH_3$=10 kg/h $CO_2$=8 kg/h $H_2O$=296 kg/h

Urea=1000 kg/h

Total=1314 kg/h

The small quantities of ammonia and carbon dioxide still present are easily recovered and recycled to the reaction step.

The process for the synthesis of urea described above is characterized by a conversion of $CO_2$ to urea i.e. a molar ratio (urea produced)/(total $CO_2$ fed), equal to 0.81. The liquid stream discharged from the reactor R1 and sent to the stripper is characterized by a molar ratio Urea/$CO_2$=4.4. Although lower than the value obtained in the previous example 1, this ratio is still surprisingly higher than that normally obtained for an analogous stream in a traditional plant, having a value of about 1.6. In addition, in this particular case there is a considerable simplification of the plant necessary for carrying out the present process.

EXAMPLE 3

A process for the synthesis of urea according to the present invention operates in such a way that the reaction for the formation of urea takes place in two distinct zones, the second of which operates at a lower temperature with the prevalent formation of carbamate, and basically coincides with the condenser which collects the gases coming from the stripper. Step (c) is carried out under autostripping conditions. Reference is made to the diagram shown in FIG. 3.

743 kg/h of fresh $CO_2$ and 631 kg/h of fresh $NH_3$ (the latter used as fluid for the ejector E2), containing a total of 13 kg/h of inert products, are fed respectively from lines 1b and 10b to the reactor-condenser R2-C2, operating at 150 ata and about 155° C. The gaseous stream of the line coming from the primary reactor R1, is fed to the same reactor condenser R2-C2 and contains:

$NH_3$=349 kg/h $CO_2$=166 kg/h $H_2O$=48 kg/h

Inert products=13 kg/h

Total=576 kg/h

The effluent 8 from R2-C2 is sent (without the intermediate ejector E1) to the phase separator FS2 and then to the primary reactor R1 via lines 13 and 11a which join line 18, having the following composition:

$NH_3$=1054 kg/h $CO_2$=860 kg/h $H_2O$=59 kg/h

Urea=60 kg/h

Total=2033 kg/h

A gaseous stream containing all the inert products leaves the top of FS2, via line 12, and these are flushed (line 12a, at 130° C.), together with a small quantity of $NH_3$ after passing through the condenser C1. The condensed part is recirculated to R1 by means of the previously mentioned line 13.

The liquid stream discharged from the overflow of the reactor R1 at a temperature of 198° C. (operating temperature of the reactor), is sent to the stripper S1 by means of line 4. It contains all the urea produced and is characterized in particular by:

Urea=1000 kg/h
$H_2O$=337 kg/h
$CO_3$=168 kg/h
$NH_3$=468 kg/h
Total=1973 kg/h

Under the above conditions, the mixture in the reactor R1 comprises a considerable vapour phase which produces the gaseous stream 3, having the composition specified above, which is sent to the reactor-condenser R2-C2.

Stream 6 rich in urea leaving the bottom of the stripper S1 (at a temperature of 205° C.) is sent to the subsequent section P for the purification and concentration of the urea, this basically consisting, in this particular case, of typical separation sections at medium and low pressure, and the concentration section which characterizes the traditional SNAMPROGETTI Urea Process of which the general outline is provided, for example on page 561 of the publication "Encyclopedia of Chemical Technology", previously mentioned. Stream 6 consists of:

$NH_3$=450 kg/h
$CO_2$=75 kg/h
$H_2O$=445 kg/h
Urea=1000 kg/h
Total=1970 kg/h

From the purification and concentration section P, an aqueous stream 5 is recovered, rich in carbamate and consisting in particular of:

$H_2O$=150 kg/h
$CO_2$=75 kg/h
$NH_3$=250 kg/h
Total=475 kg/h which is all sent again to the stripper S1 through line 5a which is joined to the stream 4 leaving the reactor.

A stream of $NH_3$ as such of 200 kg/h is recovered contemporaneously from the same section P through line 9, which is joined to the fresh ammonia coming from line 2 and sent through the ejector E1, to the condenser C2.

The process for the synthesis of urea described above is characterized by a conversion of $CO_2$ to urea, i.e., a molar ratio (urea produced)/(total $CO_2$ fed), equal to 0.81. The liquid stream discharged from the reactor R1 and sent to the stripper is characterized by a molar ratio Urea/$CO_2$=4.4. Also in this case, it is possible to greatly simplify the plant necessary for carrying out the present process, as well as to considerably increase the conversion.

EXAMPLE 4

Referring to the scheme of the enclosed FIG. 4, 580 and 452 kg/h of carbon dioxide and ammonia respectively (having an overall content of 13 kg/h of inert products) are sent to the reactor from lines 1a and 10 (this latter involving the ejector E2).

The stripper S1 operates at about 149 ata and with a temperature at the bottom of about 205° C. (with a supply with high pressure steam of about 83,000 Kcal/h); the gaseous stream 7 (863 kg/h) discharged from the head of the stripper S1 is sent to the reactor-condenser R2-C2, which operates at the above pressure (or a little lower one, due to the losses of pressure in the equipment and lines in use) and at about 145° C. (with the production of low pressure steam equivalent to about 278,000 Kcal/h). At the upper outlet of the separator FS2, cooled to 100° C., a stream of inert products 12a is obtained, consisting of:

$NH_3$=6 kg/h
inert products $(N_2+O_2)$=13 kg/h
total=19 kg/h which is sent to a subsequent recovery step (not considered in the balance).

The carbamate-containing liquid stream 8a, at the bottom of the separator FS2, consists of:

$CO_2$=220 kg/h
$NH_3$=630 kg/h
$H_2O$=32 kg/h
inert products=0.3 kg/h
total=882.3 kg/h and is sent via ejector E2 to the reactor R1 to be converted into urea The reactor for this purpose operates at 203° C. and a pressure equal to 150 ata. A valuable amount of vapour is formed in the reactor in such conditions.

The liquid phase 4 discharged from the overflow through the bottom of the reactor consists of:

urea=774 kg/h
$CO_2$=71 kg/h
$NH_3$=293 kg/h
$H_2O$=224 kg/h
total=1362 kg/h and is sent to the stripper S1 in countercurrent with a gaseous phase discharged from the top of the same reactor through line 3, consisting of:

$CO_2$=149 kg/h
$NH_3$=343 kg/h
$H_2O$=42 kg/h
inert products=13 kg/h
total=547 kg/h A stream 6, practically not containing carbamate, is discharged from the bottom of the stripper, consisting of:

urea=779 kg/h
$CO_2$=5 kg/h

Numerous variations and modifications of the process described above are possible, and although not specifically mentioned or described herein, are still available to the medium expert in the art and should be considered as forming an integral part of the present invention.

I claim:

1. In a process for the synthesis of urea from ammonia and carbon dioxide with the formation of ammonium carbamate as intermediate, comprising:
   (a) reacting, in a reaction step, ammonia and carbon dioxide at a total pressure of between 90 and 250 ata, with a molar ratio $NH_3/CO_2$ as such or in the form of ammonium carbamate, of between 2.1 and 10, with the formation of a first liquid mixture containing urea, ammonium carbamate, water and ammonia;
   (b) transferring said first liquid mixture to at least one decomposition-stripping step;
   (c) heating said first liquid mixture in said decomposition-stripping step, operating essentially at the same pressure used in the previous step (a), to obtain the decomposition of at least a part of the ammonium carbamate into ammonia and carbon dioxide, and simultaneously subjecting said liquid mixture to a stripping with the formation of a first gaseous mixture containing ammonia and carbon dioxide, and a second liquid mixture containing urea, water, ammonia and the non-decomposed part of the ammonium carbamate;

(d) transferring at least a part of said first gaseous mixture to at least one condensation step operating essentially at the same pressure as step (a) and condensing the transferred mixture with the formation of a third liquid mixture containing ammonium carbamate, water and ammonia;

(e) transferring said third liquid mixture and the remaining part of the first gaseous mixture to the reaction step (a);

(f) recovering the urea contained in the second liquid mixture in one or more subsequent decomposition, condensation and separation steps to obtain essentially pure urea and recycling to the synthesis the non-converted ammonia and carbon dioxide or in the form of ammonium carbamate; the improvement wherein:

the above reaction step (a) is carried out in two distinct zones, communicating with each other and maintained essentially at the same pressure, of which the first operates at temperature of between 170° and 230° C. with the formation of the first liquid mixture and a second prevalently gaseous mixture containing ammonia, water, carbon dioxide and optionally inert gases, and the second zone operates at a lower temperature than the first, so that at least 5% by weight of the second prevalently gaseous mixture, with respect to the weight of the above first liquid mixture is transferred from the first to the second zone, with the subsequent formation, in the latter, of a further liquid mixture containing, ammonia, ammonium carbamate and, optionally, also urea, which is again transferred from the second to the first reaction zone.

2. Process according to claim 1, wherein the condensation step (d) takes place in a condenser operating at a temperature of between 140° and 180° C.

3. Process according to either claim 1 or 2, wherein in step (a), the second prevalently gaseous mixture transferred from the first to the second reaction zone, represents from 20 to 40% by weight with respect to the weight of the first liquid mixture.

4. Process according to claim 1, wherein in step (a), the pressure is within the range of 130 to 180 ata.

5. Process according to claim 1, wherein the temperature of any of the liquid mixtures containing ammonium carbamate is maintained at a value higher than 130° C.

6. Process according to claim 1, wherein said firs reaction zone operates at temperatures of between 190° and 210° C., with molar ratios ammonia/carbon dioxide in the total feeding of between 2.5 and 4.5.

7. Process according to claim 1, wherein said second reaction zone operates at a temperature of between 140° and 200° C., with a temperature difference, with respect to the fist zone, of between 5° and 60° C.

8. Process according to claim 1, wherein, in said second reaction zone, there is the formation of urea.

9. Process according to claim 1, wherein the first liquid mixture and second prevalently gaseous mixture are taken as a single biphasic mixture from the first reaction zone, and are subsequently separated and transferred to the second reaction zone and decomposition-stripping step (c) respectively.

10. Process according to claim 1, wherein the first reaction zone comprises a first reactor and the second reaction zone comprises a second reactor preceded by a condenser on the feeding line of the prevalently gaseous mixture coming from the first reactor.

11. Process according to claim 10, wherein the average residence times in the second reactor are between 5 and 35 minutes and the temperature is between 160° and 185° C.

12. Process according to claim 1, wherein the first reaction zone comprises a first reactor and the second reaction zone comprises an exchanger-dephlagmator.

13. Process according to claim 12, wherein said exchanger-dephlagmator is equipped, on the bottom, with a stack-plate communicating with the first reactor below.

14. Process according to either of the previous claims 12 or 13, wherein the contact times in the dephlagmator are between 0.2 and 5 minutes and the temperature is between 150° and 170° C.

15. Process according to claim 1, wherein the first reaction zone comprises a first reactor and the second reaction zone comprises a second reactor consisting of an exchanger-condenser.

16. Process according to claim 15, wherein said exchanger-condenser coincides with the condenser of the condensation step (d), and operates with temperatures of between 150° and 170° C. and contact times of between 0.2 and 5 minutes.

17. Process according to claim 1, wherein the decomposition-stripping step (c) is carried out in a stripper which operates at a temperature of between 160° and 220° C. and is heated by means of indirect vapour at high pressure.

18. Process according to anyone of the previous claims, wherein the decomposition-stripping step (c) is carried out in two pieces of equipment in series, optionally of different types and operating under different conditions from each other.

19. Process according to anyone of the previous claims, wherein the feeding to the decomposition-stripping step is partialized at different heights of the stripper.

20. Process according to anyone of the previous claims, wherein the decomposition-stripping step (c) is carried out under autostripping conditions.

21. Process according to claim 1, wherein the decomposition-stripping step (c) comprises a stripper to which a gaseous mixture coming from reaction step (a), is fed as stripping agent.

22. Process according to claim 1, wherein the decomposition-stripping step (c) comprises a stripper to which said second prevalently gaseous mixture from the first zone of reaction step (a) is fed from below as a stripping agent, before entering the second reaction zone.

23. Process according to claim 22, wherein said second reaction zone coincides with the condenser of the condensation step (d), and operates with temperatures of between 150° and 170° C. and contact times of between 0.2 and 5 minutes.

24. Process according to anyone of the previous claims 22 or 23, wherein said second liquid mixture leaving the stripper contains less than 5% of carbamate.

25. Process according to claim 1, wherein the first gaseous mixture produced in step (c) has a water content of between 0.5 and 10% by weight of the total weight of the mixture.

26. Process according to claim 1, wherein from 5 to 50% of the first gaseous mixture produced in step (c) is transferred as such directly to the reaction step (a).

27. Process according to claim 1, wherein, in the step (f) for the recovery and purification of urea, a liquid recycling stream is produced, containing ammonium carbamate, water and ammonia.

28. Process according to claim 1, wherein at least a part, of the recycled liquid mixture coming from step (f) is fed to the decomposition-stripping step (c).

29. Method for improving an existing process for the production of urea starting from ammonia and carbon dioxide with the intermediate formation of ammonium carbamate, which operates with a synthesis section at high pressure, comprising:

a first synthesis reactor of urea operating with an excess of ammonia at pressure of between 90 and 250 ata, with the formation of an outgoing liquid stream containing urea, water, ammonia and the ammonium carbamate;

a decomposition step of the ammonium carbamate in said liquid stream and separation step, with stripping, of a gaseous stream containing carbon dioxide and ammonia thus formed, situated downstream from said reactor; and a condenser of the gaseous stream leaving said stripping, with the formation of a liquid stream containing ammonium carbamate fed, as a recycled product, to said first reactor, characterized in that it comprises the following operations:

(i) setting up a second reactor for the formation of ammonium carbamate, and optionally, urea starting from carbon dioxide and ammonia in excess, operating essentially at the same pressure as the above first reactor, and this second reactor may also coincide with the above existing carbamate condenser;

(ii) setting up suitable elements and connection lines for transfer of matter from the top of the above first reactor to the second reactor, and the corresponding transfer of matter from the second reactor to the first;

(iii) establishing the operating conditions of said first and second reactors so that the temperature of the second reactor is lower, than the temperature of the first, with the formation, in the latter, of a vapour phase mixed with the liquid phase;

(iv) transferring, from the top of the first reactor to the second, a gaseous or prevalently gaseous stream containing carbon dioxide and ammonia, in a quantity of at least 5% by weight, with respect to the weight of the liquid stream leaving the first reactor, with the subsequent formation, in the second reactor, of a liquid mixture containing ammonium carbamate and, optionally also urea, which is transferred to the first reactor.

30. Method according to claim 29, wherein the second reactor is preceded by a condenser on the feeding line of the prevalently gaseous mixture coming from the first reactor.

31. Method according to claim 30, wherein the average residence times in the second reactor are between 5 and 35 minutes and the temperature is between 160° and 185° C.

32. Method according to claim 29, wherein the second reactor is an exchanger-dephlagmator, equipped, on the bottom, with a stack-plate communicating with the first reactor below.

33. Method according to claim 32, wherein the contact times in the exchanger-dephlagmator are between 0.2 and 5 minutes and the temperature is between 150° and 170° C.

34. Method according to claim 29, wherein the second reactor is an exchanger-condenser, which operates with temperature of between 150° and 170° C. and contact times of between 0.2 and 5 minutes.

35. Process according to claim 1, wherein the molar ratio $NH_3/CO_2$ is between 2.1 and 6.0.

36. Process according to claim 1, wherein at least 10% by weight of the second prevalently gaseous mixture is transferred from the first to the second zone.

37. Process according to claim 7, wherein the second reaction zone operates at a temperature of between 150° and 185° C.

38. Process according to claim 12, wherein the exchanger-dephlagmator is situated at the top of the first reactor.

39. Process according to claim 21, wherein the gaseous mixture comes from the second zone of reaction step (a).

40. Process according to claim 21, wherein the stripping agent is fed from below.

41. Process according to claim 26, wherein transfer is to the first reaction zone of reaction step (a).

42. Process according to claim 28, wherein 50-100% of the recycled liquid mixture is fed to the decomposition-stripping step (c).

43. Process according to claim 29, wherein in operation (i), the temperature is between 140° and 200° C.

44. Process according to claim 29, wherein in operation (i), the temperature is between 140° and 185° C.

45. Process according to claim 29, wherein in operation (iii), the temperature of the second reactor is 5° to 60° C. lower.

46. Process according to claim 29, wherein in operation (iv), at least 10% by weight of the gaseous or prevalently gaseous stream is transferred from the first reactor to the second.

47. Process according to claim 29, wherein in operation (iv), between 20 and 40% by weight of the gaseous or prevalently gaseous stream is transferred from the first reactor to the second.

48. Process according to claim 29, wherein the liquid mixture is transferred to the first reactor from below.

49. Process according to claim 32, wherein the exchanger-dephlagmator is situated at the top of the first reactor.

50. Process according to claim 34, wherein the exchanger-condenser coincides with the condenser of the gaseous stream leaving the stripping step.

51. Process according to claim 22, wherein from 5 to 50% of the first gaseous mixture produced in step (c) in transferred as such directly to the first reaction zone of the reaction step (a).

52. Process according to claim 51, wherein the second reaction zone comprises an exchanger-condenser coincident with the condenser of said condensation step (d).

53. Process according to claim 51, wherein from 50 to 100% of the recycled liquid mixture coming from step (f) is fed to the decomposition-stripping step (c).

54. Process according to claim 52, wherein from 50 to 100% of the recycled liquid mixture coming from step (f) is fed to the decomposition-stripping step (c).

* * * * *